US00PP12549P2

(12) United States Plant Patent
Flemer, III

(10) Patent No.: US PP12,549 P2
(45) Date of Patent: Apr. 16, 2002

(54) *HAMAMELIS MOLLIS* PLANT NAMED '5473'

(75) Inventor: William Flemer, III, Plainsboro Township, Middlesex County, NJ (US)

(73) Assignee: Treesearch, Allentown, NJ (US)

( * ) Notice: Subject to any disclaimer, the term of this patent is extended or adjusted under 35 U.S.C. 154(b) by 0 days.

(21) Appl. No.: 09/562,374

(22) Filed: May 1, 2000

(51) Int. Cl.[7] ..... A01H 5/00
(52) U.S. Cl. ..... Plt./226

(58) Field of Search ..... Plt./226

*Primary Examiner*—Bruce R. Campell
*Assistant Examiner*—Susan B. McCormick
(74) *Attorney, Agent, or Firm*—James A. Lucas; Driggs, Lucas, Brubaker & Hogg Co., LPA

(57) ABSTRACT

A new cultivar of *Hamamelis mollis* plant is characterized by exceptionally large and abundant flowers with a rich fruity fragrance. It is also unique in that the leaves promptly drop in the fall, not persisting in an unsightly condition throughout the winter as in ordinary *Hamamelis mollis* seedlings.

2 Drawing Sheets

BACKGROUND OF THE INVENTION

This invention relates to a Hamamelis which is a product of crossing a seed parent *Hamamelis mollis* 'Fragrant Yellow' (not patented) with an unknown pollen parent. The plant was discovered in a row of seedlings grown from seed of the Chinese Witch-Hazel 'Fragrant Yellow'. I first grew this plant in potted understocks of *Hamamelis virginiana* common Witch-Hazel in a nursery in Plainsboro Township, N.J. in 1988. I asexually reproduced the plant by means of grafting of understocks at Plainsboro Twp. in New Jersey in January of 1991. I have observed the plants thus produced and find that the characteristics initially observed are in fact reproduced in successive generations.

The Hamamelis family includes a varied and diversified group of shrubs grown for their ornamental value. They are appreciated for their small yellow or red flowers that have a distinct fragrance when fully opened. The fruit is pod like and dry at maturity, and is characterized by its ability to split at maturity with explosive force, flinging seeds up to 40 feet from the plant.

BRIEF SUMMARY OF THE INVENTION

The *Hamamelis mollis* of this invention is distinguishable from the sister seedlings because of its exceptionally large and abundant flowers with a rich fruity fragrance. It is also unique in that the leaves promptly drop in the fall, not persisting in an unsightly condition throughout the winter as in ordinary *Hamamelis mollis* seedlings.

DESCRIPTION OF THE DRAWINGS

This new variety of Hamamelis is illustrated by the accompanying photographic drawings and depicts at 12 year old specimen of the plant by the best possible color representation using color photography. The color definitions in the specification have been taken from the Munsell Color Chart. While the colors depicted are believed to be of a high level of color fidelity, the coloration of this plant should be understood to be approximate and somewhat variable as a function of climate and the cultural conditions and horticultural practices of the grower. For example, the leaf coloration may vary depending on the composition and the concentration of fertilizer that may be applied to the plant.

BOTANICAL DESCRIPTION

Figure 1:
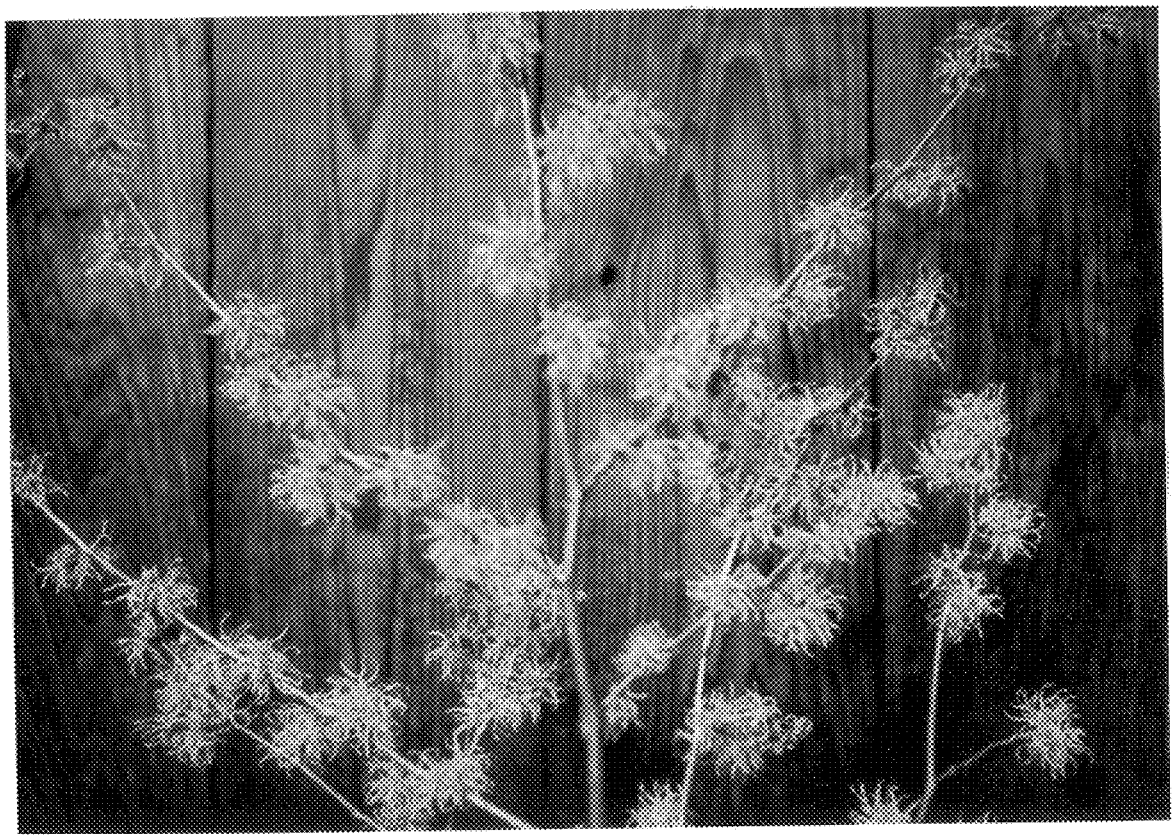
FIG. 1 is a view showing several branches of the shrub.
Figure 2:
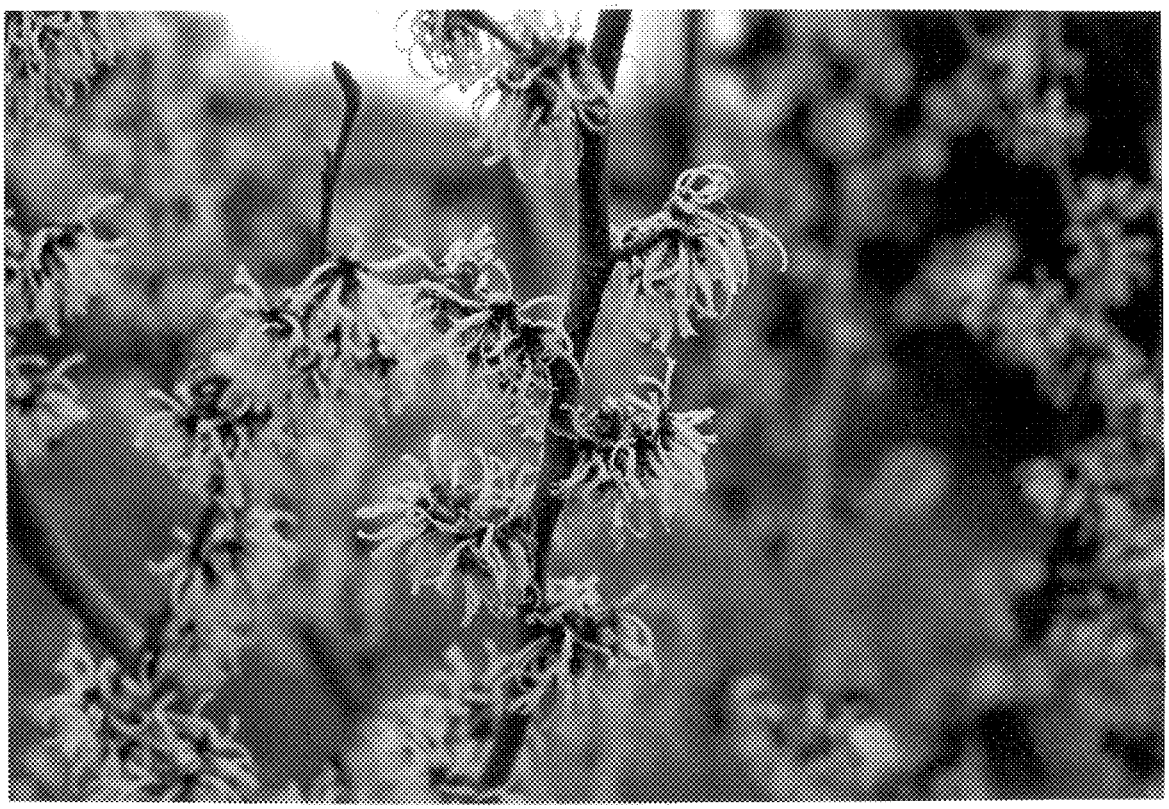
FIG. 2 is a view showing a close-up of the flowers.

Description of New Variety *Hamamelis mollis* 'February Gold'.

Where originated: On property of Princeton Nurseries in Plainsboro Township, N.J.

When originated: Fall 1988.

How originated: Seedling of *Hamamelis mollis* 'Fragrant Yellow'.

By who originated: William Flemer III.

When and how and where first propagated: January 1991 by grafting to potted understocks of *Hamamelis virginiana* at Princeton Nurseries, Plainsboro Township, N.J.

Where specimens described were grown: Plainsboro Township, N.J.

Parentage:
- *Seed parent.*—*Hamamelis mollis*, 'Fragrant Yellow'.
- *Pollen parent.*—Unknown.

Plant: Shrub.
- *Spread.*—Approximately 1.5 m at maturity.
- *Height.*—Approximately 2 m at maturity.
- *Hardiness.*—Cold hardy to 10° F. — very frost tolerant.
- *Growth.*—Vigorous upright branching, small, spreading, low.

Trunk:
- *Texture.*—Smooth.
- *Slender.*—4.5 cm in diameter.
- *Color.*—Munsell moderate brown 7.5 YR 4/5.

Branches:
- *Slender.*—0.75 cm in a diameter.
- *Length.*—Approximately 25 cm.
- *Texture.*—Smooth, pubescent for the first year.
- *Color.*—Moderate yellowish brown — 10YR 4/4.
- *Crotch angle.*—42°.
- *Lenticels.*—Sparse, small — 0.2 cm. Color: Munsell strong yellowish brown 10 YR 5/6. Number: 1 per cm of branch length. Size: 0.75 cm in diameter.

Foliage:
- *Quantity.*—Moderately abundant.
- *Arrangement.*—Alternate.

*Length*.—12 to 16 cm.
*Width*.—8–10 cm.
*Thickness*.—Thick.
*Shape*.—Obovate, short acuminate tip, obliquely cordate at base.
*Color*.—Upper surface — moderate green olive — 2.5GY 5/5. Lower surface-strong yellow green — 2.5GY 6/8.
*Texture*.—Densely tomentose on under side. Smooth matte surface on upper side.
*Disease resistance*.—No noticeable foliage disease.
*Attitude*.—Horizontal.
*Margin*.—Entire, moderately sinuate toward the terminal end.
*Petiole*.—Short, 0.2 cm long. Color: Munsell moderate yellow-green 2.5 GY 5/5.
*Glands*.—None.
*Stipules*.—Minute — 0.2 cm long.

Flower buds:
*Hardiness*.—Very hardy.
*Size*.—0.5 cm. long by 0.3 cm wide, borne on short, densely pubescent petioles.
*Shape*.—Globular.
*Color*.—Strong yellowish brown — 10YR 5/6.
*Sepals*.—Minute — 0.2 cm long.
*Calyx*.—Shape — very shallow funnel. Size — Small, 0.3 cm. wide, 0.1 cm. deep. Aspect — Smooth minutely tomentose on the outside surface. Odor — No odor when rubbed. Color — Munsell dark red 5 R 3/7.
*Peduncle*.—Length — Short — 0.5 cm long; bloom long before leaves unfold. Surface texture — Minutely downy. Opening — Buds open simultaneously about February in daylight. Not affected by adverse conditions.

Flowers:
*Dates first bloom*.—February $1^{st}$ to $15^{th}$; full bloom: February $15^{th}$ to March $15^{th}$.
*Quantity*.—Abundant.
*Size*.—Flowers on observed plant are 4 cm to 5 cm across, about twice the size of normal Hamamelis flowers.
*Borne*.—4 per flat cluster 4–5 cm. across.
*Stems*.—Very short — 0.2 cm; strong. Color — Munsell moderate yellow green 2.5 GY 5/5.
*Form*.—First open flat slightly cupped, then wide spreading. Permanence — Retains its form to the end.
*Arrangement*.—4 or 5 flowers per cluster.

Petalage:
*Number of petals*.—4 in single row.
*Shape of petals*.—Strap shaped.
*Length*.—2.5 cm.
*Color*.—Petals color vivid yellow — 2.5 Y 8/12. Flower center — Munsell dark red 5 R 3/7; calyx Munsell moderate red — 2.5R 4/10.
*Petals in center*.—None.
*Persistence*.—Drop off cleanly after lasting up to 30 days.
*Fragrance*.—Richly fragrant.
*Lastingness*.—On plant — very long up to 30 days. As cut flower — long 6 days.
*Appearance*.—Inside — Satiny. Outside: Shiny.
*Texture*.—Thin, leathery. Not affected by wet weather. Not affected by hot weather — blooming complete before hot weather.
*Arrangement*.—Regular, arranged in opposite pairs — four petals per flower.

Fruit: Dry two valved capsule.
*When borne*.—Summer, splitting open in late October.
*Abundance*.—Moderately abundant — average 550–600 flowers per plant — varies by age and size of plant.
*Size*.—1.5 cm. long, 1 cm. wide.
*Color*.—Moderate olive-brown — 2.5Y 4/4.
*Variety*.—Fertile.
*Form*.—Ovoid; flat headed; oblong shaped seeds, paired inside, tomentose, Dry two valved capsule.
*Aspect*.—Hairy tomentose — seeds inside are black, shiny, oval, flat headed and 1.3 cm long by 0.4 cm wide.
*Sepals*.—Long lasting.

Reproductive organs:
*Stamens*.—4. Anthers — very small. Color — strong, greenish, yellow — 10Y 8/11. Arrangement — Tucked in calyx. Filaments — Threads — Very short. Color — Strong greenish yellow — 7.5 Y 7/9.
*Pollen*.—Color — Strong greenish yellow — 7.5Y 7/9.
*Pistil*.—Style — Paired, very short — 1 cm. long.
*Stigmas*.—Color — Brilliant yellow-green — 2.5 GY.
*Ovaries*.—All enclosed in calyx.

What is claimed is:

1. A new cultivar of *Hamamelis mollis* plant characterized by exceptionally large and abundant flowers with a rich fruity fragrance, and rapid abscission of its leaves in autumn.

* * * * *

UNITED STATES PATENT AND TRADEMARK OFFICE

CERTIFICATE OF CORRECTION

PATENT NO. : PP 12,549 P2
DATED : April 16, 2002
INVENTOR(S) : William Flemer, III It is certified that error appears in the above-identified patent and that said Letters Patent is hereby corrected as shown below:

Title page,
Item [54], please amend the title to read as follows: -- HAMAMELIS MOLLIS NAMED 'February Gold' --

Column 1,
Line 34, change "at" to -- a --.

Signed and Sealed this

Twenty-fourth Day of September, 2002

*Attest:*

*Attesting Officer*

JAMES E. ROGAN
*Director of the United States Patent and Trademark Office*